United States Patent
Sigurani et al.

(10) Patent No.: US 12,419,822 B2
(45) Date of Patent: Sep. 23, 2025

(54) COMPOSITIONS BASED ON ALKANES AND ESTER(S) WITH TEMPERATURE STORAGE STABILITY, USE THEREOF AS SOFTENING AGENTS AND EMULSIONS COMPRISING SAME

(71) Applicants: SOCIETE D'EXPLOITATION DE PRODUITS POUR LES INDUSTRIES CHIMIQUES SEPPIC, Paris (FR); TOTAL MARKETING SERVICES, Puteaux (FR)

(72) Inventors: Séverine Sigurani, Castres (FR); Sabrina Mizael, La Garenne Colombes (FR)

(73) Assignee: TOTALENERGIES ONETECH, Courbevoie (FR)

( * ) Notice: Subject to any disclaimer, the term of this patent is extended or adjusted under 35 U.S.C. 154(b) by 752 days.

(21) Appl. No.: 17/598,704

(22) PCT Filed: Mar. 11, 2020

(86) PCT No.: PCT/FR2020/050503
§ 371 (c)(1),
(2) Date: Sep. 27, 2021

(87) PCT Pub. No.: WO2020/193900
PCT Pub. Date: Oct. 1, 2020

(65) Prior Publication Data
US 2022/0142886 A1 May 12, 2022

(30) Foreign Application Priority Data

Mar. 28, 2019 (FR) ........................ 1903276

(51) Int. Cl.
| | | |
|---|---|---|
| A61K 8/37 | (2006.01) | |
| A61K 8/06 | (2006.01) | |
| A61K 8/31 | (2006.01) | |
| A61Q 17/04 | (2006.01) | |
| A61Q 19/00 | (2006.01) | |

(52) U.S. Cl.
CPC .............. *A61K 8/375* (2013.01); *A61K 8/062* (2013.01); *A61K 8/31* (2013.01); *A61Q 17/04* (2013.01); *A61Q 19/00* (2013.01)

(58) Field of Classification Search
CPC .......... A61K 8/375; A61K 8/062; A61K 8/31; A61Q 17/04; A61Q 19/00
See application file for complete search history.

(56) References Cited

U.S. PATENT DOCUMENTS

| | | | |
|---|---|---|---|
| 5,087,445 A | 2/1992 | Haffey | |
| 2002/0085982 A1* | 7/2002 | Dorf | A61K 8/37 424/63 |
| 2012/0095120 A1 | 4/2012 | Braun | |
| 2016/0015609 A1* | 1/2016 | Merat | C08F 2/24 424/59 |
| 2018/0116946 A1 | 5/2018 | Taillebois | |
| 2019/0083369 A1 | 3/2019 | Dondeyne | |
| 2020/0113790 A1 | 4/2020 | Cambos | |

FOREIGN PATENT DOCUMENTS

| | | |
|---|---|---|
| CN | 102378624 A | 3/2012 |
| CN | 105102070 A | 11/2015 |
| CN | 107530271 A | 1/2018 |
| EP | 0 971 683 A1 | 1/2000 |
| EP | 1 832 274 A1 | 9/2007 |
| EP | 2 644 188 A1 | 10/2013 |
| JP | H0639272 B2 | 5/1994 |
| JP | 2008024610 A | 2/2008 |
| JP | 2014001206 A | 1/2014 |
| WO | 98/44902 A1 | 10/1998 |
| WO | 2008/155060 | 12/2008 |
| WO | 2011/065771 A2 | 6/2011 |
| WO | 2017/042213 | 3/2017 |
| WO | 2017191382 A1 | 11/2017 |
| WO | 2018/109354 | 6/2018 |
| WO | 2018109353 A1 | 6/2018 |

OTHER PUBLICATIONS

Pepe et al., "International Cosmetic Ingredient Dictionary and Handbook," vol. 4, Ninth Edition, 2002, pp. 2930-2936.
Michael and Irene Ash, "The Thesaurus of Chemical Products," Chemical Publishing Co. Inc., 1986, vol. I, p. 211.
Office Action issued in European Patent Application No. 20 725 876.5 dated Oct. 13, 2022.
International Search Report for PCT/FR2020/050503, mailed Jun. 24, 2020, 5 pages.
Written Opinion of the ISA for PCT/FR2020/050503, mailed Jun. 24, 2020, 6 pages.
Search Report for FR1903276, dated Jan. 31, 2020, 7 pages.
Watson, "What is Caprylic/Capric Triglyceride and Is It Safe?" Feb. 21, 2019, 4 pages.
CosmeticsDesign, SEPPIC wins the Gold best ingredient award for EMOGREEN, Dec. 5, 2016, URL: www.cosmeticsdesign.com/Product-innovations/SEPPIC-wins-the-Gold-best-ingredient-award-for-EMOGREEN, p. 1.

\* cited by examiner

*Primary Examiner* — Shirley V Gembeh
(74) *Attorney, Agent, or Firm* — NIXON & VANDERHYE

(57) ABSTRACT

Composition including, for 100 wt. % thereof: a) from 30 wt. % to 80 wt. % of at least one ester chosen from the elements of the group consisting of:—the compounds of formula (I): {CH 3-(CH 2) x1-C(=O)—O—CH 2-CH[O—C(=O)—(CH 2) x2-CH 3]-CH 2-O—C(=O)—(CH2) x3-CH 3 (I) with x1, x2 and x3 representing an integer between 6 and 8, and of—the compounds of formula (II): R—C(=O)—O—R'(II), where: R—C(=O) represents an acyl radical including from eight to ten carbon atoms, and W represents an alkyl radical including from one to twenty-two carbon atoms, and b) from 20 wt. % to 70 wt. % of at least one mixture of hydrocarbons of which at least 94 wt % includes from fifteen to nineteen carbon atoms, and oil-in-water emulsions, water-in-oil emulsions including such a composition.

14 Claims, No Drawings

COMPOSITIONS BASED ON ALKANES AND ESTER(S) WITH TEMPERATURE STORAGE STABILITY, USE THEREOF AS SOFTENING AGENTS AND EMULSIONS COMPRISING SAME

This application is the U.S. national phase of International Application No. PCT/FR2020/050503 filed 11 Mar. 2020, which designated the U.S. and claims priority to FR Patent Application No. 1903276 filed 28 Mar. 2019, the entire contents of each of which are hereby incorporated by reference.

BACKGROUND OF THE INVENTION

Field of the Invention

The present invention relates to a composition for topical use comprising at least one mixture of saturated, cyclic or acyclic, linear or branched, hydrocarbons and at least one fatty acid ester, exhibiting the properties of remaining clear, colorless and odorless after storage at different temperatures.

The present invention also relates to the use of said composition and to the cosmetic formulations for topical use comprising it.

Description of the Related Art

Many cosmetic formulations for topical use are intended to protect the skin, mucus membranes and scalp from external and environmental attacks and stresses. For example, consumers are looking for formulations to be applied to the skin which will protect it from the harmful and unsightly effects of prolonged exposure to the ultraviolet radiation of the sun, or which will prevent against detrimental change to the integrity of their skin following increasingly frequent exposure to pollutants present in atmospheres, and more particularly urban atmospheres. To meet these demands aimed at maintaining and/or at restoring the integrity of the skin in the face of identified external elements or natural aging, the cosmetics and dermocosmetics industries have over the past few decades developed new specific ingredients for improving the performance qualities required by consumers.

Furthermore, consumers are also waiting for properties of sensory and esthetic natures provided by cosmetic and dermocosmetic compositions, which give them both feelings of well-being during and after application to the skin, and also an identification with an external appearance of the cosmetic or dermocosmetic formulation, reflecting a criterion of quality. Thus, consumers are looking for cosmetic or dermocosmetic compositions which provide skin comfort during and after application to the skin. This feeling of comfort is reinforced when the step of spreading the cosmetic or dermocosmetic composition is easy, namely when its duration is reduced or more specifically is not prolonged as a consequence of resistance on the skin during said spreading, and/or when the consumer has to apply a high shear force on the skin, which is also expressed by a higher speed of application on spreading and/or by the affixing of a force having higher intensity during said spreading phase.

In specific cases, such as, for example, those of cosmetic or dermocosmetic formulations intended for the prevention against the undesired effects (redness, erythema and burns) of the ultraviolet radiation of the sun on the skin or those of creams intended for anti-inflammatory and antirheumatic treatments by the local route, which are characterized by difficulties in carrying out the spreading, it has been observed that consumers are less rigorous in carrying out the procedures for application of said protection or care products. They thus often apply too little product and/or at a frequency which is not sufficiently maintained, and this then results in a lesser protection of the skin than that forecast in the information sheet and/or on the packaging. Thus, in order to encourage better and more frequent application of these prevention and protection formulations for the skin, it is important for said formulations to exhibit pleasant sensory properties and to be able to be spread on the skin uniformly and rapidly, without involving too great an application intensity. Furthermore, consumers are looking for cosmetic or dermocosmetic formulations which do not detrimentally affect the external appearance of the skin, such as, for example, by leaving an oily residue in the form of a thin film, and, on the contrary, a cosmetic or dermocosmetic formulation which confers a matt appearance on the skin will be preferred and sought.

Taking these requirements into consideration, a person skilled in the art has available a category of ingredients called "emollients", consisting of chemical substances and chemical compositions, which can be combined with the other ingredients present in cosmetic or dermocosmetic formulations for topical use.

In the context of the present invention, "emollient agent" denotes chemical substances or chemical compositions which confer, on the formulation containing them, the properties of softening the surface of human skin after application. Such "emollient agents" are described in the work the International Cosmetic Ingredient Dictionary and Handbook, Vol. 4 ($9^{th}$ ed., 2002), and more particularly on pages 2930-2936. The disclosure of the International Cosmetic Ingredient Dictionary and Handbook, Vol. 4, pages 2930-2936, is incorporated by reference in the present patent application.

The European patent application published under the number EP 2 644 188 A1 discloses emulsions of oil-in-water type exhibiting improved properties of spreading on the skin, comprising a combination of at least one crosslinked and nonemulsifying silicone resin, at least one polyvinyl alcohol, a thickener of polyacrylamide type, an oil chosen from the elements of the group consisting of triglyceride-type vegetable oils, waxes, ethoxylated fatty alcohols, fatty acid esters, fatty acids, fatty alcohols, silicone oils and perfluorinated oils.

The international application published under the number WO 2011/065771 discloses and teaches the spreading and the softness provided during the application of an emulsion of water-in-oil-in-water type, prepared from an emulsion of water-in-oil type comprising a silicone-based emulsifier, an emulsifier of di-polyhydroxyalkylate type, an inorganic thickener of hectorite type, and a polar oil.

These solutions of the state of the art describe an improvement in the spreading properties of an emulsion by employing silicone compounds and other surfactants for which a person skilled in the art seeks an alternative in an approach where sustainable development is taken into account, and more particularly in an approach where use is made of ingredients which do not emit and/or the manufacture of which does not involve volatile organic compounds (VOCs) and/or where use is made of biodegradable ingredients according to the regulatory standards in force and/or where use is made of ingredients of plant and no longer fossil origin.

More specifically, silicone derivatives, such as chemical substances and compositions of the polysiloxane family, are known to provide improved sensory properties to oil-in-water emulsions and in particular in terms of ease of spreading and of limitation of lipid residues on the skin after application. However, the environmental characteristics associated with these ingredients have required the search for substitutes which provide similar sensory properties while having environmental characteristics in accordance with the regulations in force and to come, and in accordance with the requirements of consumers on the subject.

A partially satisfactory alternative has been demonstrated, by the use of alkane compositions comprising large amounts of cycloalkanes for preparing oil-in-water cosmetic emulsions; said alkane mixtures exhibiting biodegradability properties which are satisfactory and sensory properties which are satisfactory but judged to have room for improvement.

Recent advances have been disclosed in the international patent application published under the number WO 2018/109354 A1, and consist of the use of a mixture of saturated, cyclic or acyclic, linear or branched, hydrocarbons comprising from fifteen to nineteen carbon atoms to prepare emulsions of oil-in-water type, the sensory and esthetic properties and more particularly the spreading, consistency and richness properties of which are improved.

However, the worldwide marketing of these mixtures of saturated, cyclic or acyclic, linear or branched, hydrocarbons comprising from fifteen to nineteen carbon atoms comes up against customs constraints (Directives 2008/118/EC and 2003/96/EC). This is because these mixtures are subject to excise regulations in Europe by being put into the same category as motor fuels or heating fuels. To prevent this regulation from applying to a mixture of emollient agents, it proves to be necessary for said mixture to comprise a content by weight of less than or equal to 70% of saturated, cyclic or acyclic, linear or branched, hydrocarbons comprising from fifteen to nineteen carbon atoms.

Consequently, there exists a need to develop emollient agents:
which retain their organoleptic characteristics during their storage at different temperatures (25° C. and 45° C.) for a defined period (three months), and more particularly which remain single-phase, clear, colorless and odorless after such storage conditions, and
which make it possible, by their incorporation in cosmetic or dermocosmetic formulations, to improve the sensory properties thereof, and
the constitution of which does not involve a customs classification requiring the payment of excise Directives 2008/118/EC and 2003/96/EC.

SUMMARY OF THE INVENTION

The inventors have thus sought to develop a new solution for improving the sensory properties of emulsions of oil-in-water type and of water-in-oil type for topical use, not necessarily employing silicone derivatives but employing chemical compositions of plant and/or biodegradable origins.

This is why, according to a first aspect, a subject matter of the invention is a composition (C1) comprising, per 100% of its weight:
a) from 30% by weight to 80% by weight, preferably from 31% by weight to 80% by weight and more preferably from 31% by weight to 50% by weight of at least one ester chosen from the elements of the group consisting of:

the compounds of formula (I):

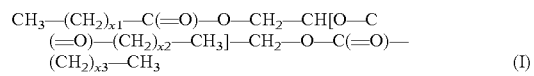

(I)

with $x_1$, $x_2$ and $x_3$ representing an integer between 6 and 8, and of
the compounds of formula (II):

$$R—C(=O)—O—R' \qquad (II)$$

with:
R—C(=O) represents an acyl radical comprising from eight to ten carbon atoms, and
R' represents an alkyl radical comprising from one to twenty-two carbon atoms,
and
b) from 20% by weight to 70% by weight, preferably from 20% by weight to 69% by weight and more particularly still from 50% by weight to 69% by weight of at least one mixture (M1) of hydrocarbons, among which at least 94% by weight comprise from fifteen to nineteen carbon atoms.

It should be noted that:
$x_1$, $x_2$ and $x_3$ can be identical or different,
the acyl and alkyl radicals can be saturated or unsaturated, linear or branched, and
the hydrocarbons of the mixture (M1) can be cyclic or acyclic, linear or branched.

As the case may be, the composition (C1) according to the invention can exhibit one or more of the following characteristics:
in the formula (I), $x_1$, $x_2$ and $x_3$ represent identical integers equal to 6, 7 or 8,
in the formula (I), $x_1$, $x_2$ and $x_3$ represent an integer which is identical and equal to 6. According to this specific aspect, the formula (I) represents glyceryl trioctanoate (CAS number=538-23-8), —in the formula (I), $x_1$, $x_2$ and $x_3$ represent an integer which is identical and equal to 8. According to this specific aspect, the formula (I) represents glyceryl tridecanoate (CAS number=621-71-6),
the composition (C1) comprises a mixture of two compounds of formula (I), preferably a mixture of glyceryl trioctanoate and of glyceryl tridecanoate and more preferentially a mixture of equal weights of glyceryl trioctanoate and of glyceryl tridecanoate,
in the formula (II), R—C(=O) represents a saturated and linear acyl radical comprising from eight to ten carbon atoms,
in the formula (II), R' represents a saturated and linear alkyl radical comprising from one to twenty-two carbon atoms, preferably from three to twenty-two carbon atoms, more preferentially from three to eighteen carbon atoms and more preferentially still from eight to eighteen carbon atoms,
the compounds of formula (II) are chosen from ethyl octanoate, propyl octanoate, isopropyl octanoate, butyl octanoate, pentyl octanoate, hexyl octanoate, octyl octanoate, nonyl octanoate, decyl octanoate, undecyl octanoate, dodecyl octanoate, tetradecyl octanoate, hexadecyl octanoate, octadecyl octanoate, ethyl nonanoate, propyl nonanoate, isopropyl nonanoate, butyl nonanoate, pentyl nonanoate, hexyl nonanoate, octyl nonanoate, nonyl nonanoate, decyl nonanoate, undecyl nonanoate, dodecyl nonanoate, tetradecyl nonanoate, hexadecyl nonanoate, octadecyl nonanoate, ethyl decanoate, propyl decanoate, isopropyl decanoate, butyl decanoate, pentyl decanoate, hexyl decanoate, octyl decanoate, nonyl decanoate, decyl decanoate, undecyl decanoate, dodecyl decanoate, tetradecyl decanoate, hexadecyl decanoate or octadecyl decanoate, in the formula (II), R—C(=O) represents a saturated and linear acyl radical comprising from eight to ten carbon atoms and R' represents a saturated and linear alkyl radical comprising from eight to eighteen carbon atoms, in the formula (II), R—C(=O) represents a saturated and linear acyl radical chosen from the elements of the group consisting of the octanoyl radical, the nonanoyl radical and the decanoyl radical, and R' represents a saturated and linear alkyl radical chosen from the elements of the group consisting of the n-octyl radical, the n-decyl radical, the n-dodecyl radical, the n-tetradecyl radical, the n-hexadecyl radical and the n-octadecyl radical, the formula (II) represents one of the elements chosen from the members of the group consisting of octyl octanoate, nonyl octanoate, decyl octanoate, undecyl octanoate, dodecyl octanoate, tetradecyl octanoate, hexadecyl octanoate, octadecyl octanoate, octyl decanoate, nonyl decanoate, decyl decanoate, undecyl decanoate, dodecyl decanoate, tetradecyl decanoate, hexadecyl decanoate and octadecyl decanoate, the formula (II) represents the product of the esterification reaction between an equimolar mixture of octanoic acid and of decanoic acid and coconut alcohol, the formula (II) represents the product sold under the INCI name Coco-Caprylate/Caprate (CAS number=95912-86-0), said mixture (M1) comprises, per 100% of its weight, a proportion by weight of branched alkanes of greater than or equal to 80% and less than or equal to 100%, preferably of greater than or equal to 90%; a proportion by weight of linear alkanes of greater than or equal to 0% and less than or equal to 15%, preferably of less than or equal to 10%; and a proportion by weight of cycloalkanes of greater than or equal to 0% and less than or equal to 5%, preferably of less than or equal to 1%, said mixture (M1) is a mixture of saturated hydrocarbons sold under the brand name Emogreen™ L15 comprising, per 100% of its weight:

3.7% of linear alkanes comprising from fifteen to nineteen carbon atoms,

96% of isoalkanes comprising from fifteen to nineteen carbon atoms, and 0.3% of cycloalkanes comprising from fifteen to nineteen carbon atoms, said mixture (M1) is a mixture of saturated hydrocarbons sold under the brand name Emogreen™ L19 comprising, per 100% of its weight:

3.8% of linear alkanes comprising from fifteen to nineteen carbon atoms, 96.2% of isoalkanes comprising from fifteen to nineteen carbon atoms, and a proportion by weight of less than 0.1% of cycloalkanes comprising from fifteen to nineteen carbon atoms, said mixture (M1) is a mixture of saturated hydrocarbons sold under the brand name Emogreen™ L19 also comprising, per 100% of its weight, 15% to 20% by weight of alkanes (linear, isoalkanes and cycloalkanes) comprising 17 carbon atoms, 70% to 75% by weight of alkanes (linear, isoalkanes and cycloalkanes) comprising 18 carbon atoms and 4% to 6% by weight of alkanes (linear, isoalkanes and cycloalkanes) comprising 19 carbon atoms.

Within the meaning of the present invention, "coconut alcohol" is understood to mean the product of the hydrogenation of a mixture of fatty acids originating from the saponification of a coconut oil and which comprises, per 100% of its weight:

from 5% to 10% by weight of octanoic acid from 5% to 10% by weight of decanoic acid from 43% to 53% by weight of dodecanoic acid from 15% to 21% by weight of tetradecanoic acid from 7% to 21% by weight of hexadecanoic acid from 2% to 4% by weight of octadecanoic acid.

Within the meaning of the present invention, "linear alkanes" present in the mixture ($M_1$) included in the composition (C1) which is a subject matter of the present invention and comprising from fifteen to nineteen carbon atoms more particularly denotes the elements chosen from the group consisting of n-pentadecane, n-hexadecane, n-heptadecane, n-octadecane and n-nonadecane.

Within the meaning of the present invention, "branched alkanes" (or isoalkanes) present in the mixture ($M_1$) included in the composition (C1) which is a subject matter of the present invention and comprising from fifteen to nineteen carbon atoms more particularly denotes the elements chosen from the group consisting of 2-methyltetradecane (or isopentadecane), 2-methylpentadecane (or isohexadecane), 2-methylhexadecane (or isoheptadecane), 2-methylheptadecane (or isooctadecane) and 2-methyloctadecane (or isononadecane).

Within the meaning of the present invention, cycloalkanes present in the mixture ($M_1$) included in the composition (C1) which is a subject matter of the present invention and comprising from fifteen to nineteen carbon atoms more particularly denotes saturated hydrocarbons comprising at least one saturated cyclic hydrocarbon group optionally substituted by one or more linear or branched alkyl radicals.

It should be noted that the composition (C1) which is a subject matter of the present invention and as defined above can be prepared by mixing at least one ester chosen from the group consisting of the compounds of formula (I) and the compounds of formula (II) with a mixture (M1) as defined above, at a temperature of between 20° C. and 60° C., and under mechanical stirring equipped with a rotor of anchor or turbine type, at a speed of between 20 revolutions/minute and 500 revolutions/minute.

Another subject matter of the invention is a composition (E1) for topical use existing in the form of an emulsion of oil-in-water type, characterized in that it comprises, per 100% of its weight:

a) from 50% to 90% by weight, preferably from 60% to 90% by weight and more preferentially still from 70% to 90% by weight of a cosmetically acceptable aqueous phase (A1), b) from 10% to 50% by weight, preferably from 10% to 40% by weight and more preferentially still from 10% to 30% by weight of a fatty phase (G1) comprising, per 100% of its weight:

$b_{11}$) from 10% to 80% by weight, preferably from 10% to 70% by weight, of a composition ($C_1$) according to the invention;

$b_{12}$) from 0.5% to 20% by weight, preferably from 1% to 15%, of at least one surface-active agent of oil-in-water type (S1), $b_{13}$) from 0% to 89.5% by weight of at least one oil and/or one wax with a composition different from the composition (CA with the sum of the proportions by weight of $b_{11}$), $b_{12}$) and $b_{13}$) equal to 100% of the fatty phase (G1).

The expression "for topical use" used in the definition of the composition (E1) which exists in the form of an emulsion of oil-in-water type as defined above, means that said composition is employed by application to the skin, the hair, the scalp or the mucus membranes, whether it is a direct application in the case of a cosmetic, dermocosmetic, dermopharmaceutical or pharmaceutical composition or an indirect application, for example in the case of a body hygiene product in the form of a textile or paper wipe or of health products intended to be in contact with the skin or the mucus membranes.

The expression "cosmetically acceptable" used in the definition of the aqueous phase ($A_1$) of the composition (E1) existing in the form of an emulsion of oil-in-water type means, according to the Council of the European Economic Community Directive 76/768/EEC of Jul. 27, 1976, amended by Directive 93/35/EEC of Jun. 14, 1993, any substance or preparation intended to be placed in contact with the various parts of the human body (epidermis, hair system, nails, lips and genital organs) or with the teeth and the mucus membranes of the oral cavity with a view exclusively and mainly to cleaning them, perfuming them, changing their appearance and/or correcting their body odors and/or protecting them or keeping them in good condition. A cosmetically acceptable medium of these compositions which are a subject matter of the invention can conventionally contain water, one or more cosmetically acceptable organic solvents, or a mixture of water and of one or more organic solvents. The cosmetically acceptable solvents can more particularly be chosen from polyhydric alcohols, such as, for example, glycerol, diglycerol, glycerol oligomers, ethylene glycol, propylene glycol, hexylene glycol, diethylene glycol, xylitol, erythritol, sorbitol, or water-soluble alcohols.

Within the meaning of the present invention, "oil" present in the fatty phase ($G_1$) of the composition (E1) existing in the form of an emulsion of oil-in-water type as defined above denotes chemical substances or mixtures of chemical substances which are insoluble in water and which exist under a liquid appearance at a temperature of 25° C.

Within the meaning of the present invention, "wax" present in the fatty phase ($G_1$) of the composition (E1) existing in the form of an emulsion of oil-in-water type as defined above denotes chemical substances or mixtures of chemical substances which are insoluble in water and which exist under a solid appearance at a temperature of 45° C.

Within the meaning of the present invention, "surface-active agent of oil-in-water type (S1)" present in the fatty phase ($G_1$) of the composition (E1) existing in the form of an emulsion of oil-in-water type as defined above denotes the chemical substance or the mixture of chemical substances which makes it possible to stabilize the droplets of said fatty phase ($G_1$) in dispersion in the continuous aqueous phase ($A_1$).

Mention may be made, as surface-active agent of oil-in-water type (S1) present in the fatty phase (G1) of the emulsion ($E_1$) of oil-in-water type as defined above, for example, of:

polysorbates resulting from the ethoxylation reaction between one molar equivalent of sorbitan esters and between 5 and 20 molar equivalents of ethylene oxide, and more particularly between one molar equivalent of sorbitan laurate or of sorbitan palmitate or of sorbitan stearate or of sorbitan isostearate or of sorbitan oleate and between 5 and 20 molar equivalents of ethylene oxide;

the products resulting from the ethoxylation reaction between one molar equivalent of a fatty acid, such as, for example, palmitic acid, myristic acid, lauric acid, stearic acid, isostearic acid or oleic acid, and between 5 to 40 molar equivalents of ethylene oxide;

the products resulting from the esterification reaction between a fatty acid, such as, for example, palmitic acid, myristic acid, lauric acid, stearic acid, isostearic acid, oleic acid, arachidic acid or behenic acid, and between 4 to 20 molar equivalents, more particularly between 3 to 10 molar equivalents, of glycerol.

Within the meaning of the present invention, "fatty phase (G1)" denotes a fatty substance or a mixture of fatty substances which is insoluble in water and/or in mixtures of water and of polar solvents. Such a "fatty phase" can comprise oils and/or waxes as defined above and not meeting the definition of the composition (C1). Mention may be made, among the constituent elements of the fatty phase (G1), of:

oils of animal origin, such as squalene or squalane;

vegetable oils, such as phytosqualane, sweet almond oil, coconut oil, castor oil, jojoba oil, olive oil, rapeseed oil, peanut oil, sunflower oil, wheatgerm oil, corn germ oil, soybean oil, cottonseed oil, alfalfa oil, poppy oil, pumpkin seed oil, evening primrose oil, millet oil, barley oil, rye oil, safflower oil, candlenut oil, passionflower oil, hazelnut oil, palm oil, shea butter, apricot kernel oil, calophyllum oil, sisymbrium oil, avocado oil, calendula oil, sesame oil, meadowsweet oil, macadamia kiwi oil, borage oil, blackcurrant seed oil, coffee oil, pistachio oil, peach kernel oil, raspberry seed oil, strawberry seed oil, melon oil, blueberry seed oil, argan oil, oily plum extract, pomegranate oil, papaya oil, coconut milk oil, oils resulting from flowers or vegetables;

ethoxylated vegetable oils;

synthetic oils, such as fatty acid esters not corresponding to the definition of the formula (II), such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, esters derived from lanolic acid, such as isopropyl lanolate or isocetyl lanolate, glycerol triheptanoate, alkylbenzoates, hydrogenated oils, poly-α-olefins, polyolefins, such as polyisobutene, hydrogenated polydecene or hydrogenated polyisobutene, sold in France by Ets B. Rossow et Cie under the name Parleam—Polysynlane™, cited in: Michel and Irene Ash; Thesaurus of Chemical Products, Chemical Publishing Co. Inc., 1986, Volume I, page 211 (ISBN 0 7131 3603 0);

silicone oils, such as polydimethylsiloxanes, polymethylphenylsiloxanes, silicones modified by amines, silicones modified by fatty acids, silicones modified by alcohols, silicones modified by alcohols and fatty acids, silicones modified by polyether groups, epoxy-modified silicones, silicones modified by fluorinated groups, cyclic silicones and silicones modified by alkyl groups;

waxes, such as beeswax, carnauba wax, candelilla wax, ouricury wax, Japan wax, cork fiber wax, sugar cane wax, jojoba wax, blackcurrant flower wax, narcissus flower wax, orange blossom wax, orange wax, rice wax, lignite waxes, microcrystalline waxes, lanolin wax; ozokerite; polyethylene wax, silicone waxes; vegetable waxes; fatty alcohols and fatty acids which are solid at ambient temperature; glycerides which are solid at ambient temperature.

According to a specific aspect, in the composition (E1) which is a subject matter of the present invention, the fatty phase (G1) additionally comprises, per 100% of its own weight: $b_{14}$) from 5% to 30% by weight, more particularly from 5% to 25% by weight and more particularly still from 10% to 25% by weight of at least one agent for protecting against the ultraviolet radiation of the sun,
with the sum of the proportions by weight of b 1), $b_{12}$), $b_{13}$) and $b_{14}$) equal to 100% of the fatty phase (G1).

The agent for protecting against the ultraviolet radiation of the sun will preferably be chosen from the elements of the group consisting of titanium dioxide, 2,4-dihydroxybenzophenone, 2-(4-diethylamino-2-hydroxybenzoyl)benzoic acid hexyl ester, 2,4-bis[4-(2-ethylhexyloxy)-2-hydroxyphenyl]-6-(4-methoxyphenyl)-1,3,5-triazine, 2,4,6-tris[4-(2-ethylhexyloxycarbonyl)anilino]-1,3,5-triazine and 2-ethylhexyl dimethoxybenzylidene dioxoimidazolidine propionate.

Agent for protecting against the ultraviolet radiation of the sun denotes in particular, in the definition of the composition (E1) for topical use which exists in the form of an emulsion of oil-in-water type and which is a subject matter of the present invention, pigments, organic sunscreens and inorganic sunscreens.

Examples of pigments used as agent for protecting against the ultraviolet radiation of the sun are titanium dioxide, brown iron oxides, yellow iron oxides, black iron oxides or red iron oxides or also white or colored pearlescent pigments, such as titanium oxide-coated micas.

Examples of organic sunscreens used as agent for protecting against the ultraviolet radiation of the sun are:
those of the family of the derivatives of benzoic acid, such as para-aminobenzoic acids (PABAs), in particular monoglycerol esters of PABA, ethyl esters of N,N-propoxy-PABA, ethyl esters of N,N-diethoxy-PABA, ethyl esters of N,N-dimethyl-PABA, methyl esters of N,N-dimethyl-PABA, butyl esters of N,N-dimethyl-PABA;
those of the family of the derivatives of anthranilic acid, such as homomenthyl N-acetylanthranilate;
those of the family of the derivatives of salicylic acid, such as amyl salicylate, homomenthyl salicylate, ethylhexyl salicylate, phenyl salicylate, benzyl salicylate, p-isopropanolphenyl salicylate;
those of the family of the derivatives of cinnamic acid, such as ethylhexyl cinnamate, ethyl 4-isopropylcinnamate, methyl 2,5-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl di-para-methoxy mono-2-ethylhexanoyl cinnamate;
those of the family of the derivatives of benzophenone, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2-carboxylate, 2-hydroxy-4-(n-octyloxy)benzophenone, 4-hydroxy-3-carboxybenzophenone; 3-4'-methylbenzylidene-d,l-camphor, 3-benzylidene-d,l-camphor, camphor benzalkonium methosulfate; urocanic acid, ethyl urocanate;
those of the family of the derivatives of sulfonic acid, such as 2-phenylbenzimidazole-5-sulfonic acid and its salts; the family of the derivatives of triazine, such as hydroxyphenyl triazine, ethylhexyloxyhydroxyphenyl-4-methoxyphenyltriazine, 2,4,6-trianilino-(p-carbo-2'-ethylhexyl-1'-oxy)-1,3,5-triazine, the 4,4-((6-(((1,1-dimethylethyl)amino)carbonyl)phenyl)amino)-1,3,5-triazine-2,4-diyl diimino) bis(2-ethylhexyl) ester of benzoic acid, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole; dibenzazine; dianisoylmethane, 4-methoxy-4"-t-butylbenzoylmethane; 5-(3,3-dimethyl-2-norbornylidene)-3-pentan-2-one; 2-(4-diethylamino-2-hydroxybenzoyl)benzoic acid hexyl ester, 2,4-bis[4-(2-ethylhexyloxy)-2-hydroxyphenyl]-6-(4-methoxyphenyl)-1,3,5-triazine, 2,4,6-tris[4-(2-ethylhexyloxycarbonyl)anilino]-1,3,5-triazine, 2-ethylhexyl dimethoxybenzylidene dioxoimidazolidine propionate, the family of the derivatives of diphenylacrylate, such as 2-ethylhexyl 2-cyano-3,3-diphenyl-2-propenoate or ethyl 2-cyano-3,3-diphenyl-2-propenoate;
those of the family of the polysiloxanes, such as benzylidene siloxane malonate.

Examples of inorganic sunscreens used as agent for protecting against the ultraviolet radiation of the sun are: titanium oxides, zinc oxides, cerium oxide, zirconium oxide, yellow, red or black iron oxides, chromium oxides. These inorganic screening agents may or may not be micronized, may or may not have undergone surface treatments and may optionally be presented in the form of aqueous or oily predispersions.

According to another aspect, a subject matter of the invention is a composition (E1) according to the invention for protecting human skin against the unsightly effects of exposure to the ultraviolet radiation of the sun, and more particularly against redness.

According to another aspect, a subject matter of the invention is a composition (E1) according to the invention for treating or slowing down a detrimental change to the skin due to burns, sunburn, erythema or cancer.

According to a more specific aspect, a subject matter of the invention is a composition (E1) as defined above, characterized in that the fatty phase (G1) additionally comprises at least, per 100% of its own weight:
$b_{14}$) from 5% to 15% by weight of at least one colored pigment (CP),
with the sum of the proportions by weight of $b_{11}$), $b_{12}$), $b_{13}$) and $b_{14}$) equal to 100% of the fatty phase (G1).

Another subject matter of the invention is a composition (E2) for topical use existing in the form of an emulsion of water-in-oil type, characterized in that it comprises, per 100% of its weight:
a) from 60% to 98% by weight, preferably from 60% to 95% by weight, preferentially from 60% to 90% by weight and more preferentially still from 60% to 85% by weight of a cosmetically acceptable aqueous phase (A2),
b) from 2% to 40% by weight, preferably from 5% to 40% by weight, more preferentially from 10% to 40% by weight and more preferentially still from 15% to 40% by weight of a fatty phase (G2) comprising, per 100% of its weight:

b$_{21}$) from 10% to 80% by weight, preferably from 10% to 70% by weight, of a composition (C$_1$);

b$_{22}$) from 0.5% to 20% by weight, preferably from 1% to 15% by weight, of at least one surface-active agent of water-in-oil type (S2), b$_{23}$) from 0% to 89.5% by weight of at least one oil and/or one wax with a composition different from the composition (CA and with the sum of the proportions by weight of b$_{21}$), b$_{22}$) and b$_{23}$) equal to 100% of the fatty phase (G2).

Within the meaning of the present invention, "oil" present in the fatty phase (G$_2$) of the composition (E2) existing in the form of an emulsion of water-in-oil type as defined above denotes chemical substances or mixtures of chemical substances which are insoluble in water and which exist under a liquid appearance at a temperature of 25° C.

Within the meaning of the present invention, "wax" present in the fatty phase (G$_2$) of the composition (E2) existing in the form of an emulsion of water-in-oil type as defined above denotes chemical substances or mixtures of chemical substances which are insoluble in water and which exist under a solid appearance at a temperature of 45° C.

Mention will in particular be made, among the emulsifying surfactants of water-in-oil type (S2) capable of being used in the context of the present invention, of lipoamino acids and their salts; lipopeptides and their salts; sorbitan esters, such as, for example, sorbitan laurate, sorbitan palmitate, sorbitan stearate, sorbitan oleate, sorbitan sesquioleate, sorbitan trioleate, sorbitan isostearate; polyglycerol esters, such as, for example, glycerol laurate, glycerol palmitate, glycerol stearate, glycerol oleate, glycerol sesquioleate, glycerol trioleate, glycerol isostearate, diglycerol laurate, diglycerol palmitate, diglycerol stearate, diglycerol oleate, diglycerol sesquioleate, diglycerol trioleate, diglycerol isostearate; alkylpolyglycosides, compositions of alkylpolyglycosides and of fatty alcohols, esters of polyglycerols or of polyglycols or of polyols, such as polyhydroxystearates of polyglycols or of polyglycerol, such as, for example, the products denoted Hypermer® B246, Arlacel® P135 sold by Uniqema, the product denoted Dehymuls® PGPH sold by Cognis, the product denoted Decaglyn® 5HS sold by Nikko; polyethylene glycol-alkyl glycol copolymers, such as PEG-45 dodecyl glycol copolymer, such as the product sold under the name Elfacos ST 9® by Akzo; sucrose esters, ethoxylated or nonethoxylated methylglucoside esters; ethoxylated fatty acids; ethoxylated fatty alcohols; anionic emulsifiers, such as decyl phosphate or cetearyl sulfate; aluminum polyoxystearate, such as, for example, the product sold under the name Manalox® by Rhodia; magnesium stearate; aluminum stearate.

According to a more specific aspect, the emulsifying agent of water-in-oil type (S2) is chosen from the compositions of alkylpolyglycosides, the compositions of alkylpolyglycosides and of fatty alcohols, the esters of polyglycerols, the esters of alkoxylated polyglycerols, the polyhydroxystearates of polyglycols, the polyhydroxystearates of polyglycerols, the polyhydroxystearates of alkoxylated polyglycerols, the polyethylene glycol-alkyl glycol copolymers.

Within the meaning of the present invention, "cosmetically acceptable aqueous phase (A2)" denotes an aqueous phase having the same definition as the aqueous phase (A1).

According to a specific aspect, in the composition (E1) which is a subject matter of the present invention, the fatty phase (G2) additionally comprises, per 100% of its own weight:

b$_{24}$) from 5% to 30% by weight, more particularly from 5% to 25% by weight and more particularly still from 10% to 25% by weight of at least one agent for protecting against the ultraviolet radiation of the sun, with the sum of the proportions by weight of b$_{21}$), b$_{22}$), b$_{23}$) and b$_{24}$) equal to 100% of the fatty phase (G2).

The agent for protecting against the ultraviolet radiation of the sun will preferably be chosen from the elements of the group consisting of titanium dioxide, 2,4-dihydroxybenzophenone, 2-(4-diethylamino-2-hydroxybenzoyl)benzoic acid hexyl ester, 2,4-bis[4-(2-ethylhexyloxy)-2-hydroxyphenyl]-6-(4-methoxyphenyl)-1,3,5-triazine, 2,4,6-tris[4-(2-ethylhexyloxycarbonyl)anilino]-1,3,5-triazine and 2-ethylhexyl dimethoxybenzylidene dioxoimidazolidine propionate.

According to another aspect, a subject matter of the invention is a composition (E2) according to the invention for protecting human skin against the unsightly effects of exposure to the ultraviolet radiation of the sun, and more particularly against redness.

According to another aspect, a subject matter of the invention is a composition (E2) according to the invention for treating or slowing down a detrimental change to the skin due to burns, sunburn, erythema or cancer.

According to a more specific aspect, a subject matter of the invention is a composition (E2) as defined above, characterized in that the fatty phase (G2) additionally comprises at least, per 100% of its own weight:

b$_{24}$) from 5% to 15% by weight of at least one colored pigment (CP), with the sum of the proportions by weight of b$_{21}$), b$_{22}$), b$_{23}$) and b$_{24}$) equal to 100% of the fatty phase (G2).

Preferably, the colored pigment (CP) is chosen from the elements of the group consisting of inorganic pigments, organic pigments and pearlescent pigments.

In the case where the colored pigment (CP) is an inorganic pigment, it will preferably be chosen from the elements of the group consisting of titanium dioxide (rutile or anatase), optionally surface treated; black, yellow, red and brown iron oxides; manganese violet; ultramarine blue; optionally hydrated chromium oxide; ferric blue.

In the case where the colored pigment (CP) is an organic pigment, it will preferably be selected from the elements of the group consisting of D&C Red pigment, D&C Orange pigment, D&C Yellow pigment, carbon black, lakes based on cochineal carmine.

In the case where the colored pigment (CP) is a pearlescent pigment, it will preferably be selected from the elements of the group consisting of white pearlescent pigments, such as, for example, titanium oxide-coated mica with iron oxides, titanium oxide-coated mica with ferric blue or chromium oxide, titanium oxide-coated mica with an organic pigment, pigments based on bismuth oxychloride.

Another subject matter of the invention is a makeup method, characterized in that it comprises a stage of application, to said human skin, of a composition (E2) as defined above. Said stage of application of the composition for topical use (F) to the skin can be carried out using the fingers or an applicator, such as, for example, a brush or a sponge.

According to another aspect, another subject matter of the invention is a composition (E2) for topical use existing in the form of an emulsion of water-in-oil type and as defined above, characterized in that the aqueous phase (A2) comprises, per 100% of its own weight, from 0.5% by weight to 10% by weight, preferably from 0.5% by weight to 5% by weight and more preferentially still from 0.5% by weight to 3% by weight of at least one crosslinked anionic polyelectrolyte polymer (P).

Crosslinked anionic polyelectrolyte (P) denotes, in the definition of the composition (E2) for topical use existing in the form of an emulsion of water-in-oil type and a subject matter of the present invention, a nonlinear crosslinked anionic polyelectrolyte, existing in the form of a three-dimensional network which is insoluble in water but which can swell with water and resulting in the production of a chemical gel.

According to a specific aspect of the present invention, the crosslinked anionic polyelectrolyte (P) present in the composition (E2) comprises a proportion of greater than or equal to 25 mol % of monomer units resulting from 2-methyl-2 [(1-oxo-2-propenyl)amino]-1-propanesulfonic acid in free acid or partially or completely salified form.

According to a specific aspect, the crosslinked anionic polyelectrolyte (P) present in the composition (E2) comprises, per 100 mol %:
- (a1)—a proportion of greater than or equal to 25 mol % and of less than or equal to 100 mol % of monomer units resulting from 2-methyl-2-[(1-oxo-2-propenyl) amino]-1-propanesulfonic acid in free acid or partially or completely salified form;
- (a2)—optionally, a proportion of greater than 0 mol % and of less than or equal to 75 mol % of monomer units resulting from at least one monomer chosen from the elements of the group consisting of acrylamide, N,N-dimethylacrylamide, methacrylamide or N-isopropylacrylamide;
- (a3)—optionally, a proportion of greater than 0 mol % and of less than or equal to 20 mol %, more particularly greater than 0 mol % and of less than or equal to 15 mol %, more particularly still of greater than or equal to 0 mol % and of less than or equal to 10 mol % of monomer units resulting from at least one monomer chosen from the elements of the group consisting of 2-hydroxyethyl acrylate, 2,3-dihydroxypropyl acrylate, 2-hydroxyethyl methacrylate, 2,3-dihydroxypropyl methacrylate and vinylpyrrolidone;
- (a4)—optionally, a proportion of greater than 0 mol % and of less than or equal to 75 mol % of monomer units resulting from at least one monomer chosen from the elements of the group consisting of acrylic acid, methacrylic acid, 2-carboxyethylacrylic acid, itaconic acid, maleic acid and 3-methyl-3-[(1-oxo-2-propenyl) amino]butanoic acid, the carboxylic functional group of said monomers being in free acid, partially salified or totally salified form;
- (a5)—optionally, a proportion of greater than 0 mol % and of less than or equal to 5 mol % of at least one monomer of formula (1):

[Chem 1]

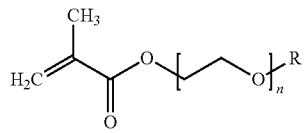

(1)

in which R represents a linear or branched alkyl radical comprising from eight to twenty carbon atoms and n represents an integer of greater than or equal to zero and of less than or equal to twenty;
- (a6)—a proportion of greater than 0 mol % and of less than or equal to 1 mol % of monomer units resulting from at least one diethylenic or polyethylenic crosslinking monomer (AR); the sum of said molar proportions as monomer units according to a1), a2), a3), a4), a5) and a6) being equal to 100 mol %.

Within the meaning of the present invention, the term "salified" indicates that the acid functional group present in a monomer is in an anionic form associated in the salt form with a cation, in particular alkali metal salts, such as sodium or potassium cations, or such as nitrogenous base cations, such as the ammonium salt, lysine salt or monoethanolamine ($HOCH_2$—$CH_2$—$NH_3$) salt. They are preferably sodium or ammonium salts.

At least one diethylenic or polyethylenic crosslinking monomer (AR) in particular denotes, in the definition of said crosslinked anionic polyelectrolyte (P), a monomer chosen from the elements of the group consisting of methylenebis (acrylamide), ethylene glycol dimethacrylate, diethylene glycol diacrylate, ethylene glycol diacrylate, diallylurea, triallylamine, trimethylolpropane triacrylate, diallyloxyacetic acid or one of its salts, such as sodium diallyloxyacetate, or a mixture of these compounds; and more particularly a monomer chosen from ethylene glycol dimethacrylate, triallylamine, trimethylolpropane triacrylate or methylenebis(acrylamide) or a mixture of these compounds.

According to another specific aspect of the present invention, the composition (E2) for topical use existing in the form of an emulsion of water-in-oil type is characterized in that said crosslinking monomer (AR) as defined above is employed in a molar proportion of less than or equal to 0.5%, more particularly of less than or equal to 0.25% and very particularly of less than or equal to 0.1%; it is more particularly greater than or equal to 0.005 mol %.

The crosslinked anionic polyelectrolyte (P) employed in the composition (E2) can also comprise various additives, such as complexing agents, transfer agents or chain-limiting agents.

The crosslinked anionic polyelectrolyte (P) employed in the composition (E2) can be prepared by the implementation of a radical polymerization process known to a person skilled in the art, such as, for example, processes of solution polymerization, of suspension polymerization, of inverse suspension polymerization, of emulsion polymerization, of inverse emulsion polymerization or of polymerization in a solvent medium, followed by a stage of precipitation of the polymer formed.

According to a more specific aspect, the crosslinked anionic polyelectrolyte (P) employed in the composition (E2) comprises can be prepared by the implementation of a process of polymerization in a solvent medium, followed by a stage of precipitation of the polymer formed, or of inverse emulsion polymerization, optionally followed by a stage of concentration and/or atomization.

According to a more specific aspect, the crosslinked anionic polyelectrolyte (P) employed in the composition the composition (E2) can be prepared according to one of the processes described above and can involve the use of transfer or chain-limiting agents. The transfer or chain-limiting agents are more particularly chosen from the group consisting of sodium hypophosphite, alcohols of low molecular weight, for example methanol, ethanol, 1-propanol, isopropanol or butanol, thiols, for example 2-mercaptoethanol, transfer agents comprising a sulfate functional group, for example sodium methallylsulfonate, or mixtures of said transfer agents. The transfer or chain-limiting agents are more particularly used in molar proportions, expressed with respect to the total number of moles of monomers employed, of 0.001 mol % to 1 mol %, more particularly of 0.001 mol % to 0.5 mol % and very particularly of 0.001 mol % to 0.1 mol %.

According to another specific aspect of the present invention, said crosslinked anionic polyelectrolyte (P) is an element of the group consisting of a homopolymer of 2-methyl-2-[(1-oxo-2-propenyl)amino]-1-propanesulfonic acid partially or completely salified in sodium salt or ammonium salt form, crosslinked by triallylamine and/or methylenebis(acrylamide); a copolymer of 2-methyl-2-[(1-oxo-2-propenyl)amino]-1-propanesulfonic acid partially or completely salified in sodium salt or ammonium salt form and of acrylic acid partially or completely salified in sodium salt or ammonium salt form, crosslinked by triallylamine and/or methylenebis(acrylamide); a copolymer of 2-methyl-2-[(1-oxo-2-propenyl)amino]-1-propanesulfonic acid ($\gamma$) partially or completely salified in sodium salt or ammonium salt form and of acrylic acid ($\delta$) partially or completely salified in sodium salt form in a molar ratio ($\gamma$)/($\delta$) of greater than or equal to 30/70 and less than or equal to 90/10, crosslinked by triallylamine and/or methylenebis(acrylamide); a copolymer of 2-methyl-2-[(1-oxo-2-propenyl)amino]-1-propanesulfonic acid ($\gamma$) partially or completely salified in sodium salt form and of acrylic acid ($\delta$) partially or completely salified in sodium salt form in a molar ratio ($\gamma$)/($\delta$) of greater than or equal to 40/60 and less than or equal to 90/10, crosslinked by triallylamine and/or methylenebis(acrylamide); a copolymer of 2-methyl-2-[(1-oxo-2-propenyl)amino]-1-propanesulfonic acid ($\gamma$) partially or completely salified in sodium salt form and of acrylamide ($\varepsilon$) in a molar ratio ($\gamma$)/($\varepsilon$) of greater than or equal to 30/70 and less than or equal to 90/10, crosslinked by triallylamine and/or methylenebis(acrylamide); a copolymer of 2-methyl-2-[(1-oxo-2-propenyl)amino]-1-propanesulfonic acid ($\gamma$) partially or completely salified in sodium salt form and of hydroxyethyl acrylate ($\zeta$) in a molar ratio ($\gamma$)/($\zeta$) of greater than or equal to 30/70 and less than or equal to 90/10, crosslinked by triallylamine and/or methylenebis(acrylamide); a terpolymer crosslinked by triallylamine and/or methylenebis(acrylamide) of 2-methyl-2-[(1-oxo-2-propenyl)amino]-1-propanesulfonic acid partially or completely salified in sodium salt or ammonium salt form, of acrylamide and of acrylic acid partially or completely salified in sodium salt or ammonium salt form; a terpolymer crosslinked by triallylamine and/or methylenebis(acrylamide) of 2-methyl-2-[(1-oxo-2-propenyl)amino]-1-propanesulfonic acid partially or completely salified in sodium salt or ammonium salt form in a molar proportion of greater than or equal to 30% and less than or equal to 45%, of acrylamide in a molar proportion of greater than or equal to 45% and less than or equal to 68% and of acrylic acid partially or completely salified in sodium salt or ammonium salt form in a molar proportion of greater than or equal to 2% and less than or equal to 10%; a terpolymer crosslinked by triallylamine and/or methylenebis(acrylamide) of 2-methyl-2[(1-oxo-2-propenyl)amino]-1-propanesulfonic acid partially or completely salified in sodium salt or ammonium salt form in a molar proportion of greater than or equal to 30% and less than or equal to 45%, of acrylamide in a molar proportion of greater than or equal to 47% and less than or equal to 68% and of acrylic acid partially or completely salified in sodium salt or ammonium salt form in a molar proportion of greater than or equal to 2% and less than or equal to 8%; a terpolymer crosslinked by trimethylolpropane triacrylate and/or triallylamine and/or methylenebis(acrylamide) of 2-methyl-2-[(1-oxo-2-propenyl)amino]-1-propanesulfonic acid partially or completely salified in sodium salt or ammonium salt form in a molar proportion of greater than or equal to 60% and less than or equal to 80%, of N,N-dimethylacrylamide in a molar proportion of greater than or equal to 15% and less than or equal to 39.5% and of tetraethoxylated lauryl methacrylate in a molar proportion of greater than or equal to 0.5% and less than or equal to 5%; a tetrapolymer crosslinked by trimethylolpropane triacrylate and/or triallylamine and/or methylenebis(acrylamide) of 2-methyl-2-[(1-oxo-2-propenyl)amino]-1-propanesulfonic acid partially or completely salified in sodium salt or ammonium salt form in a molar proportion of greater than or equal to 60% and less than or equal to 80%, of N,N-dimethylacrylamide in a molar proportion of greater than or equal to 15% and less than or equal to 39%, of lauryl methacrylate in a molar proportion of greater than or equal to 0.5% and less than or equal to 2.5% and of stearyl methacrylate in a molar proportion of greater than or equal to 0.5% and less than or equal to 2.5%.

According to a specific aspect, the composition (E2) is characterized in that the water-in-oil emulsifying surface-active agent (S2) comprises at least one composition (CA1) represented by the formula (III):

$$R_1\text{—O-}(G)_x\text{-H} \qquad (III)$$

in which x represents a decimal number of between 1.05 and 5, G represents the residue of a reducing sugar and $R_1$ represents a saturated or unsaturated, linear or branched, aliphatic hydrocarbon radical, optionally substituted with one or more hydroxyl groups, comprising from 12 to 36 carbon atoms, said composition (CA1) consisting of a mixture of compounds represented by the formulas $(III_1)$, $(III_2)$, $(III_3)$, $(III_4)$ and $(III_5)$:

$$R_1\text{—O-}(G)_1\text{-H} \qquad (III_1)$$

$$R_1\text{—O-}(G)_2\text{-H} \qquad (III_2)$$

$$R_1\text{—O-}(G)_3\text{-H} \qquad (III_3)$$

$$R_1\text{—O-}(G)_4\text{-H} \qquad (III_4)$$

$$R_1\text{—O-}(G)_5\text{-H} \qquad (III_5)$$

in the respective molar proportions $a_1$, $a_2$, $a_3$, $a_4$ and $a_5$ such that:

the sum $a_1+a_2+a_3+a_4+a_5$ is equal to 1 and that
the sum $a_1+2a_2+3a_3+4a_4+5a_5$ is equal to x.

Saturated or unsaturated, linear or branched, aliphatic hydrocarbon radical, optionally substituted with one or more hydroxyl groups, comprising from 12 to 36 carbon atoms, denotes, for the radical $R_1$ in the formula (III) as defined above:

saturated linear alkyl radicals, for example the n-dodecyl, n-tridecyl, n-tetradecyl, n-pentadecyl, n-hexadecyl, n-heptadecyl, n-octadecyl, n-nonadecyl, n-eicosyl or n-docosyl radicals;

unsaturated linear radicals, such as the dodecenyl, tridecenyl, tetradecenyl, pentadecenyl, hexadecenyl, heptadecenyl, octadecenyl, nonadecenyl, eicosenyl, docosenyl, 4-dodecenyl or 5-dodecenyl radicals;

saturated or unsaturated, linear or branched, aliphatic radicals comprising from 12 to 36 carbon atoms substituted by one or two hydroxyl groups, such as the hydroxydodecyl, hydroxytetradecyl, hydroxyhexadecyl, hydroxyoctadecyl, hydroxyeicosyl or hydroxydocosyl radicals, for example the 12-hydroxyoctadecyl radical;

radicals resulting from the isoalkanols of formula (2):

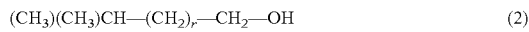

in which r represents an integer between 8 and 20, for example the isodecyl, isoundecyl, isododecyl, isotridecyl, isotetradecyl, isopentadecyl, isohexadecyl, isopentadecyl, isooctadecyl, isononadecyl, isoeicosyl or isodocosyl radicals;

branched alkyl radicals, resulting from Guerbet alcohols, of formula (3):

in which t is an integer between 6 and 18, s is an integer between 4 and 18 and the sum s+t is greater than or equal to 10 and less than or equal to 22, for example the 2-butyloctyl, 2-butyldecyl, 2-hexyloctyl, 2-hexyldecyl, 2-octyldecyl, 2-hexyldodecyl, 2-octyldodecyl, 2-decyltetradecyl, 2-dodecylhexadecyl or 2-tetradecyloctadecyl radicals.

According to a specific aspect, in the definition of the formula (III) as defined above, $R_1$ represents a saturated or unsaturated, linear or branched, aliphatic hydrocarbon radical comprising from 12 to 24 carbon atoms.

Reducing sugar, in the definition of the formula (III) as defined above, denotes the saccharide derivatives which do not exhibit, in their structures, a glycoside bond established between an anomeric carbon and the oxygen of an acetal group, as they are defined in the reference work: Biochemistry, Daniel Voet/Judith G. Voet, p. 250, John Wiley & Sons, 1990. The oligomeric structure $(G)_x$ can exist in any isomeric form, whether it is optical isomerism, geometrical isomerism or regioisomerism; it can also represent a mixture of isomers.

In the formula (II) as defined above, the group $R_1$—O— is bonded to G via the anomeric carbon of the saccharide residue, so as to form an acetal functional group.

According to a specific aspect, in the definition of the formula (III) as defined above, G represents the residue of a reducing sugar chosen from glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose; and more particularly G represents the residue of a reducing sugar chosen from the residues of glucose, xylose and arabinose.

According to an even more specific aspect, in the definition of the formula (III) representing the composition (CA1) included in the composition ($E_2$) for topical use existing in the form of an emulsion of water-in-oil type and a subject matter of the present invention, x represents a decimal number greater than or equal to 1.05 and less than or equal to 2.5, more particularly greater than or equal to 1.05 and less than or equal to 2.0 and more particularly still greater than or equal to 1.25 and less than or equal to 2.0.

According to an even more specific aspect, in the definition of the formula (III) as defined above, $R_1$ represents the radical chosen from at least one of the elements of the group consisting of the n-dodecyl, n-tetradecyl, n-hexadecyl, n-octadecyl, n-eicosyl, n-docosyl, 2-hexyldecyl, 2-octyldecyl, 2-hexyldodecyl, 2-octyldodecyl and 2-decyltetradecyl radicals, G represents the residue of a reducing sugar chosen from the residues of glucose and xylose and x represents a decimal number greater than or equal to 1.05 and less than or equal to 2.5.

According to a specific aspect, the composition (E2) is characterized in that the water-in-oil emulsifying surface-active agent (S2) comprises at least one composition (CA1) of alkylpolyglycosides which is represented by the formula (III):

in which x represents a decimal number between 1.05 and 2.5, G represents the xylose residue and $R_1$ represents the 2-octyldodecyl radical, said composition ($C_1$) consisting of a mixture of compounds represented by the formulae ($III_1$), ($III_2$), ($III_3$), ($III_4$) and ($III_5$):

in the respective molar proportions $a_1$, $a_2$, $a_3$, $a_4$ and $a_5$ such that:
the sum $a_1+a_2+a_3+a_4+a_5$ is equal to 1 and that
the sum $a_1+2a_2+3a_3+4a_4+5a_5$ is equal to x.

"G represents the xylose residue" is understood to mean "G represents the xylosyl or α,β-D-xylopyranosyl radical, obtained from the elimination of the hemiacetal hydroxyl group of β-D-xylopyranose".

According to a specific aspect, the composition (E2) as defined above is characterized in that said emulsifying agent (S2) consists of a composition (CA2) comprising, per 100% of its weight:

from 10% to 50% by weight, preferably from 15% to 40% by weight and more preferentially still from 20% to 30% by weight of the composition of alkylpolyglycosides (CA1)

and from 90% to 50% by weight, preferably from 85% to 60% by weight and more preferentially still from 80% to 70% by weight of at least one fatty alcohol of formula (IV):

with $R'_1$ identical to or different from $R_1$ and representing a saturated or unsaturated, linear or branched, aliphatic hydrocarbon radical, optionally substituted with one or more hydroxyl groups, comprising from 12 to 36 carbon atoms.

According to a specific aspect, in the definition of the formula (III) representing the composition (CA1) included in the composition (CA2), $R_1$ represents the radical chosen from the n-dodecyl, n-tetradecyl, n-hexadecyl, n-octadecyl, n-eicosyl, n-docosyl, 2-hexyldecyl, 2-octyldecyl, 2-hexyldodecyl, 2-octyldodecyl and 2-decyltetradecyl radicals, G represents the residue of a reducing sugar chosen from the residues of glucose and xylose and x represents a decimal number greater than or equal to 1.05 and less than or equal to 2.5.

According to a more specific aspect, in the definition of the formula (III) representing the composition (CA1) included in the composition (CA2), $R_1$ represents the 2-octyldodecyl radical, G represents the xylose residue and x represents a decimal number greater than or equal to 1.05 and less than or equal to 2.5.

According to a more specific aspect, in the definition of the fatty alcohol of formula (IV) as defined above, $R'_1$ represents a radical chosen from the n-dodecyl, n-tetradecyl, n-hexadecyl, n-octadecyl, n-eicosyl, n-docosyl, 2-hexyldecyl, 2-octyldecyl, 2-hexyldodecyl, 2-octyldodecyl or 2-decyltetradecyl radicals; R'₁ very particularly represents the 2-octyldodecyl radical.

According to a specific aspect, the composition (E2) as defined above is characterized in that said emulsifying agent (S2) consists of a composition (CA2) comprising, per 100% of its weight:
from 10% to 50% by weight of the composition of alkylpolyglycosides (CA1) and
from 90% to 50% by weight of at least one fatty alcohol of formula (IV):

R'₁—OH  (IV), with R'₁ representing the 2-octyldodecyl radical.

According to a specific aspect, the composition (E2) as defined above is characterized in that said emulsifying agent (S2) consists of a composition (CA3) comprising, per 100% of its weight:—from 15% to 25% by weight of the composition (CA1) and
from 55% to 65% by weight of at least one fatty alcohol of formula (IV):

R'₁—OH  (IV), in which R'₁ represents the 2-octyldodecyl radical;
from 10% to 30% by weight of at least one polyhydroxystearate of polyglycols represented by the formula (V):

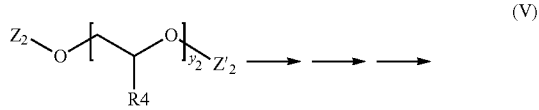
(V)

in which $y_2$ represents an integer greater than or equal to 2 and less than or equal to 50, $R_4$ represents the hydrogen atom, the methyl radical or the ethyl radical, $Z_2$ represents a radical of formula (VI):

[Chem 3]

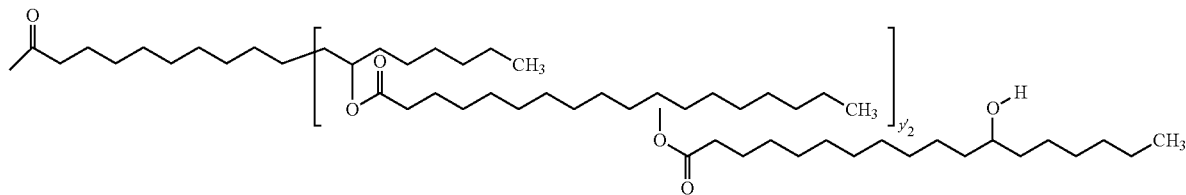
(VI)

in which $y'_2$ represents an integer greater than or equal to 0 and less than or equal to 10, more particularly greater than or equal to 1 and less than or equal to 10, and $Z'_2$ represents a radical of formula (VI) as defined above, with $Z'_2$ identical to or different from $Z_2$, or the hydrogen atom.

The compositions ($C_1$), (E1) and (E2) which are subject matters of the present invention and are as defined above are intended for a topical use, and can be incorporated in any type of cosmetic, dermocosmetic, dermopharmaceutical or pharmaceutical formulation intended for a topical use, or else in any type of support intended to be brought into contact with the skin (paper, wipe, textile, transdermal patch, and the like).

The compositions ($C_1$), (E1) and (E2) which are subject matters of the present invention and are as defined above can be packaged in the pressurized form in an aerosol device or in a device of "pump-action spray" type, in a device equipped with an openwork wall, for example a grating, or in a device equipped with a ball applicator (roll-on).

The compositions ($C_1$), (E1) and (E2) which are subject matters of the present invention and are as defined above can be used as cleansing or makeup-removing milks, as cleansing or makeup-removing lotions, as foaming gels for the face or for the body, as shampoo for cleaning the hair and/or scalp, as conditioner for the treatment of the hair and/or scalp, as foam bath, as cream, as milk or as lotion for caring for or protecting the face, hands and body, for example as agent for protecting from solar radiation, as self-tanning agent, as antiaging agent, as antiwrinkle agent, as soothing agent or as moisturizing agent.

The compositions ($C_1$), (E1) and (E2) which are subject matters of the present invention and are as defined above can additionally comprise excipients and/or active principles generally employed in the field of formulations for topical use, in particular cosmetic, dermocosmetic, pharmaceutical or dermopharmaceutical formulations.

The compositions ($C_1$), (E1) and (E2) which are subject matters of the present invention and are as defined above can additionally comprise one or more auxiliary compounds chosen from foaming and/or detergent surfactants, thickening and/or gelling surfactants, thickening and/or gelling agents, stabilizing agents, film-forming compounds, solvents and cosolvents, hydrotropic agents, plasticizing agents, emulsifying and coemulsifying agents, opacifying agents, pearlescent agents, superfatting agents, sequestrants, chelating agents, antioxidants, fragrances, essential oils, preserving agents, conditioning agents, deodorants, bleaching agents intended for bleaching bodily hair and the skin, active principles intended to contribute a treating and/or protective action with regard to the skin or the hair, sunscreens, inorganic fillers or pigments, particles which give a visual effect or which are intended for the encapsulation of active principles, exfoliant particles, texturing agents, optical brighteners or insect repellents.

Mention may be made, as examples of foaming and/or detergent surfactants optionally present in the compositions ($C_1$), (E1) and (E2) which are subject matters of the present invention, of topically acceptable foaming and/or detergent anionic, cationic, amphoteric or nonionic surfactants generally used in this field of activity.

Mention may be made, among the foaming and/or detergent anionic surfactants which can be combined with the compositions ($C_1$), (E1) and (E2) which are subject matters of the present invention, of alkali metal salts, alkaline earth metal salts, ammonium salts, amine salts or aminoalcohol salts of alkyl ether sulfates, of alkyl sulfates, of alkylamido ether sulfates, of alkylaryl polyether sulfates, of monoglyceride sulfates, of α-olefin sulfonates, of paraffin sulfonates, of alkyl phosphates, of alkyl ether phosphates, of alkyl sulfonates, of alkylamide sulfonates, of alkylaryl sulfonates, of alkyl carboxylates, of alkylsulfosuccinates, of alkyl ether sulfosuccinates, of alkylamide sulfosuccinates, of alkylsulfoacetates, of alkyl sarcosinates, of acylisethionates, of N-acyl taurates, of acyl lactylates, of N-acylated derivatives of amino acids, of N-acylated derivatives of peptides, of N-acylated derivatives of proteins, or of fatty acids.

Mention may be made, among the foaming and/or detergent amphoteric surfactants optionally present in the compositions ($C_1$), (E1) and (E2) which are subject matters of the present invention, of alkylbetaines, alkylamidobetaines, sultaines, alkylamidoalkylsulfobetaines, imidazoline derivatives, phosphobetaines, amphopolyacetates and amphopropionates.

Mention may in particular be made, among the foaming and/or detergent cationic surfactants optionally present in the compositions ($C_1$), (E1) and (E2) which are subject matters of the present invention, of quaternary ammonium derivatives.

Mention may more particularly be made, among the foaming and/or detergent nonionic surfactants optionally present in the compositions ($C_1$), (E1) and (E2) which are subject matters of the present invention, of alkylpolyglycosides comprising a saturated or unsaturated and linear or branched aliphatic radical comprising from 8 to 12 carbon atoms; castor oil derivatives, polysorbates, coconut amides, N-alkylamines.

Mention may be made, as examples of thickening and/or gelling surfactants optionally present in the compositions ($C_1$), (E1) and (E2) which are subject matters of the present invention, of:
optionally alkoxylated fatty esters of alkylpolyglycosides and very particularly ethoxylated esters of methyl polyglucoside, such as PEG 120 methyl glucose trioleate and PEG 120 methyl glucose dioleate, sold respectively under the names Glucamate™ LT and Glucamate™ DOE-120;
alkoxylated fatty esters, such as PEG 150 pentaerythrityl tetrastearate, sold under the name Crothix™ DS53, or PEG 55 propylene glycol oleate, sold under the name Antil™ 141;
carbamates of polyalkylene glycols comprising fatty chains, such as PPG 14 laureth isophoryl dicarbamate, sold under the name Elfacos™ T211, or PPG 14 palmeth 60 hexyl dicarbamate, sold under the name Elfacos™ GT2125.

Mention may be made, as examples of deodorants optionally present in the compositions ($C_1$), (E1) and (E2) which are subject matters of the present invention, of alkali metal silicates; zinc salts, such as zinc sulfate, zinc gluconate, zinc chloride or zinc lactate; quaternary ammonium salts, such as cetyltrimethylammonium salts or cetylpyridinium salts; glycerol derivatives, such as glyceryl caprate, glyceryl caprylate and polyglyceryl caprate; 1,2-decanediol; 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and of glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, or the complex of aluminum sesquichlorohydrate and of polyethylene glycol.

Mention may be made, as examples of antioxidants optionally present in the compositions ($C_1$), (E1) and (E2) which are subject matters of the present invention, of EDTA and its salts, citric acid, tartaric acid, oxalic acid, BHA (butylated hydroxyanisole), BHT (butylated hydroxytoluene), tocopherol derivatives, such as tocopherol acetate, mixtures of antioxidant compounds, such as Dissolvine GL 47S (INCI name: Tetrasodium Glutamate Diacetate).

Mention may be made, among the active principles which the compositions ($C_1$), (E1) and (E2) which are subject matters of the present invention can comprise, of:
vitamins and their derivatives, in particular their esters, such as retinol (vitamin A) and its esters (retinyl palmitate, for example), ascorbic acid (vitamin C) and its esters, sugar derivatives of ascorbic acid (such as ascorbyl glucoside), tocopherol (vitamin E) and its esters (such as tocopherol acetate), vitamins B3 or B10 (niacinamide and its derivatives); compounds showing a soothing action, in particular Sepicalm™ S, allantoin and bisabolol; anti-inflammatory agents; compounds showing a moisturizing action, such as urea, hydroxyureas, glycerol glucoside, diglycerol glucoside, polyglyceryl glucosides, glycerol, diglycerol or xylityl polyglucoside, sold under the brand name Aquaxyl™; plant extracts rich in polyphenols, such as grape extracts, pine extracts, wine extracts or olive extracts; compounds showing a slimming or lipolytic action, such as caffeine or its derivatives, Adiposlim™, Adipoless™ or fucoxanthin; N-acylated proteins; N-acylated peptides, such as Matrixil™; N-acylated amino acids; partial hydrolysates of N-acylated proteins; amino acids; peptides; total hydrolysates of proteins; soybean extracts, for example Raffermine™; wheat extracts, for example Tensine™ or Gliadine™; plant extracts, such as plant extracts rich in tannins, plant extracts rich in isoflavones or plant extracts rich in terpenes; extracts of freshwater or marine algae; extracts of marine plants; marine extracts in general, such as corals; essential waxes; bacterial extracts; ceramides; phospholipids; compounds showing an antimicrobial action or a purifying action, such as Lipacide™ CBG, Lipacide™ UG, Sepicontrol™ A5, Octopirox™ or Sensiva™ SC50; compounds showing an energizing or stimulating property, such as Physiogenyl™, or panthenol and its derivatives, such as Sepicap™ MP; antiaging active principles, such as Sepilift™ DPHP, Lipacide™ PVB, Sepivinol™, Sepivital™, Manoliva™ Phyto-Age™, Timecode™ or Survicode™; antiphotoaging active principles; active principles which protect the integrity of the dermoepidermal junction; active principles which increase the synthesis of the components of the extracellular matrix, such as collagen, elastins or glycosaminoglycans; active principles which act favorably on chemical cell communication, such as cytokines, or physical cell communication, such as integrins; active principles which create a feeling of "heating" on the skin, such as activators of cutaneous microcirculation (such as nicotinic acid derivatives) or products which create a feeling of "coolness" on the skin (such as menthol and derivatives); active principles which improve cutaneous microcirculation, for example venotonics; draining active principles; active principles having a decongestant purpose, such as extracts of *Ginko biloba*, ivy, horse chestnut, bamboo, ruscus, butcher's broom, *Centalla asiatica*, fucus, rosemary or willow; agents for tanning or browning the skin, such as, for example, dihydroxyacetone (DHA), erythrulose, mesotartaric aldehyde, glutaraldehyde, glyceraldehyde, alloxan, ninhydrin, plant extracts, such as, for example, extracts of red woods of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in the European patent application EP 0 971 683; agents known for their action in facilitating and/or accelerating the tanning and/or browning of human skin, and/or for their action in coloring human skin, such as, for example, carotenoids (and more particularly β-carotene and γ-carotene), the product sold under the brand name "Carrot oil" (INCI name: *Daucus carota, Helianthus annuus* Sunflower Oil) by Provital, which contains carotenoids, vitamin E and vitamin K; tyrosine and/or its derivatives, known for their effect on the acceleration of the tanning of human skin in combination with exposure to ultraviolet radiation, such as, for example, the product sold under the brand name "SunTan Accelerator™" by Provital, which contains tyrosine and riboflavins (vitamin B), the complex of tyrosine and of tyrosinase sold under the brand name "Zymo Tan Complex" by Zymo Line, the product sold under the brand name MelanoBronze™ (INCI name: Acetyl Tyrosine, Monks Pepper Extract (Vitex Agnus-Castus)) by Mibelle which contains acetyl tyrosine, the product sold under the brand name Unipertan VEG-24/242/2002 (INCI name: Butylene Glycol and Acetyl Tyrosine and Hydrolyzed Vegetable Protein and Adenosine Triphosphate) by Unipex, the product sold under the brand name "Try-Excell™" (INCI name: Oleoyl Tyrosine and Luffa *Cylindrica* (Seed) Oil and Oleic Acid) by Sederma which contains extracts of pumpkin seeds (or loofah oil), the product sold under the brand name "Actibronze™" (INCI name: Hydrolyzed Wheat Protein and Acetyl Tyrosine and Copper Gluconate) by Alban Muller, the product sold under the brand name Tyrostan™ (INCI name: Potassium Caproyl Tyrosine) by Synerga, the product sold under the brand name Tyrosinol (INCI name: Sorbitan Isostearate, Glyceryl Oleate, Caproyl Tyrosine) by Synerga, the product sold under the brand name InstaBronze™ (INCI name: Dihydroxyacetone and Acetyl Tyrosine and Copper Gluconate) sold by Alban Muller, the product sold under the brand name Tyrosilane (INCI name: Methylsilanol and Acetyl Tyrosine) by Exymol; peptides known for their effect in activating melanogenesis, such as, for example, the product sold under the brand name Bronzing SF Peptide powder (INCI name: Dextran and Octapeptide-5) by Infinitec Activos, the product sold under the brand name Melitane (INCI name: Glycerin and Aqua and Dextran and Acetyl Hexapeptide-1) comprising acetyl hexapeptide-1 known for its α-MSH agonist action, the product sold under the brand name Melatimes Solutions™ (INCI name: Butylene Glycol, Palmitoyl Tripeptide-40) by Lipotec, sugars and sugar derivatives, such as, for example, the product sold under the brand name Tanositol™ (INCI name: Inositol) by Provital, the product sold under the brand name Thalitan™ (or Phycosaccharide™ AG) by Codif International (INCI name: Aqua and Hydrolyzed Algin (*Laminaria Digitata*) and Magnesium Sulfate and Manganese Sulfate) containing an oligosaccharide of marine origin (guluronic acid and mannuronic acid which are chelated with magnesium and manganese ions), the product sold under the brand name Melactiva™ (INCI name: Maltodextrin, *Mucuna pruriens* Seed Extract) by Alban Muller, compounds rich in flavonoids, such as, for example, the product sold under the brand name "Biotanning" (INCI name: Hydrolyzed Citrus *Aurantium dulcis* Fruit Extract) by Silab and known to be rich in lemon flavonoids (of hesperidins type).

Mention may be made, among the texturing agents which the compositions ($C_1$), (E1) and (E2) which are subject matters of the present invention can comprise, of lauroyl lysine, sold under the name Aminohope™ LL by Ajinomoto, octenyl starch succinate, sold under the name Dryflo™ by National Starch, the myristyl polyglucoside sold by SEPPIC under the name Montanov™ 14, cellulose fibers, cotton fibers or chitosan fibers.

The process for the preparation of the composition ($E_2$) as defined above comprises the following stages:

a stage a) of preparation of the fatty phase ($G_2$) by mixing all the elements constituting it in the desired proportions. This mixing stage is generally carried out at a temperature of greater than or equal to 20° C. and less than or equal to 80° C., more particularly of greater than or equal to 20° C. and less than or equal to 60° C. and more particularly still of greater than or equal to 20° C. and less than or equal to 40° C.; it is carried out under mechanical stirring at a moderate speed of greater than or equal to 50 revolutions/minute and less than or equal to 100 revolutions/minute;

a stage b) of preparation of the aqueous phase ($A_2$) of all the elements constituting it in the desired proportions. This mixing stage is generally carried out at a temperature of greater than or equal to 20° C. and less than or equal to 80° C., more particularly of greater than or equal to 20° C. and less than or equal to 60° C. and more particularly still of greater than or equal to 20° C. and less than or equal to 40° C.; it is carried out under mechanical stirring at a moderate speed of greater than or equal to 500 revolutions/minute and less than or equal to 3000 revolutions/minute. In particular, the aqueous phase ($A_1$) obtained on conclusion of stage b) exhibits a dynamic viscosity, measured at 20° C. via a viscometer of Brookfield LV type at a speed of 6 revolutions/minute, of greater than or equal to 200 mPa·s and less than or equal to 40 000 mPa·s, more particularly of greater than or equal to 1000 mPa·s and less than or equal to 40 000 mPa·s and more particularly still of greater than or equal to 2000 mPa·s and less than or equal to 40 000 mPa·s;

a stage c) during which the fatty phase ($G_2$) is added to the aqueous phase ($A_1$) at a temperature of greater than or equal to 20° C. and less than or equal to 80° C., more particularly of greater than or equal to 20° C. and less than or equal to 60° C. and more particularly still of greater than or equal to 20° C. and less than or equal to 40° C., under mechanical stirring at a moderate speed of greater than or equal to 50 revolutions/minute and less than or equal to 400 revolutions/minute, so as to obtain the composition ($E_2$).

DESCRIPTION OF THE PREFERRED EMBODIMENTS

The following examples illustrate the invention without, however, limiting it.

A—Preparation of Compositions According to the Invention and of Comparative Compositions, Comprising a Mixture ($M_1$) and Esters.

The desired amount of the composition sold under the brand name Emogreen™ L19 is introduced into a glass reactor provided with a jacket in which a thermostatically controlled fluid circulates and with mechanical stirring provided with a stirrer equipped with a blade of anchor type. The stirring speed is regulated at 50 revolutions/minute and the temperature at 25° C. The desired amount of ester of formula (I) or of formula (II) is subsequently introduced gradually and the mixture thus obtained is homogenized at a temperature of 25° C. and at a stirring speed of 80 revolutions/minute for 30 minutes. The mixture is subsequently emptied out.

In this way, the compositions C11 and C12 according to the invention and the comparative compositions C21, C22 and C23 are obtained, the constitutions by weight of which are described in table 1 below.

Compositions C11 and C12 according to the invention and the comparative compositions C21, C22 and C23

TABLE 1

| | Composition C11 | Composition C12 | Composition C21 | Composition C22 | Composition C23 |
|---|---|---|---|---|---|
| Emogreen ™L19[1] | 70% | 70% | 70% | 70% | 70% |
| Caprylic/Capric triglycerides[2] | 30% | 0% | 0% | 0% | 0% |
| Coco caprylate caprate[3] | 0% | 30% | 0% | 0% | 0% |
| Sunflower oil[4] | 0% | 0% | 30% | 0% | 0% |
| Isocetyl Stearoyl Stearate[5] | 0% | 0% | 0% | 30% | 0% |
| Jojoba oil[6] | 0% | 0% | 0% | 0% | 30% |

[1]Emogreen ™ L19 is a mixture of saturated hydrocarbons comprising, per 100% of its weight:
i) 3.8% of linear alkanes comprising from fifteen to nineteen carbon atoms,
ii) 96.2% of isoalkanes comprising from fifteen to nineteen carbon atoms, and
iii) a proportion by weight of less than 0.1% of cycloalkanes comprising from fifteen to nineteen carbon atoms; said mixture also comprising, per 100% of its weight, 15% to 20% by weight of alkanes (linear, isoalkanes and cycloalkanes) comprising 17 carbon atoms, 70% to 75% by weight of alkanes (linear, isoalkanes and cycloalkanes) comprising 18 carbon atoms and 4% to 6% by weight of alkanes (linear, isoalkanes and cycloalkanes) comprising 19 carbon atoms.
[2]Caprylic/capric triglycerides is a mixture of equal weights of glyceryl trioctanoate and glyceryl tridecanoate
[3]Coco caprylate/caprate is a mixture obtained by esterification of a mixture of octanoic acid and decanoic acid with coconut alcohol, and more particularly the mixture sold under the brand name Lanol ™ 2681.
[4]Sunflower oil is a mixture of triglycerides, the distribution in fatty acids of which comprises, per 100% of its weight, from 5% to 7% by weight of palmitic acid, from 4% to 6% by weight of stearic acid, from 15% to 25% of oleic acid and from 62% to 72% by weight of linoleic acid.
[5]Isocetyl Stearoyl Stearate or Isohexadecyl 12-[(1-oxooctadecyl)oxy]octadecanoate (CAS number = 97338-28-8) is sold under the trade name Dub SSIC.
[6]Jojoba oil is a linear ester comprising from 36 to 46 carbon atoms.

B—Evaluation of the Stability of the Compositions C11 and C12 According to the Invention and of the Comparative Compositions C21, C22 and C23 a) An amount of 100 ml of the composition to be tested and contained in a 250 ml flask is introduced into a climate-controlled chamber regulated at 25° C., for a period of time of 3 months.

The following criteria are evaluated before stabilization in the chamber and after a period of time of three months in said climate-controlled chamber:
  Visual appearance of the composition tested
  Odor of the composition tested b) An amount of 100 ml of the composition to be tested and contained in a 250 ml flask is introduced into a climate-controlled chamber regulated at 45° C., for a period of time of 3 months.

The following criteria are evaluated before stabilization in the chamber and after a period of time of three months in said climate-controlled chamber:
  Visual appearance of the tested composition
  Odor of the tested composition c) The results obtained are recorded in the following table 2:

Organoleptic evaluation of the compositions C11 and C12 according to the invention and the comparative compositions C21, C22 and C23.

TABLE 2

|  | Appearance before storage | Appearance after 3 months at 25° C. | Appearance after 3 months at 45° C. | Odor before storage | Odor after 3 months at 25° C. | Odor after 3 months at 45° C. |
|---|---|---|---|---|---|---|
| Composition C11 | Clear colorless liquid | Clear colorless liquid | Clear colorless liquid | Odorless | Odorless | Odorless |
| Composition C12 | Clear colorless liquid | Clear colorless liquid | Clear colorless liquid | Odorless | Odorless | Odorless |
| Composition C21 | Clear colorless liquid | Clear light-yellow liquid | Clear light-yellow liquid | Odorless | Moderate intensity odor (oxidation odor) | Moderate intensity odor (oxidation odor) |
| Composition C22 | Clear colorless liquid | Clear dark-yellow liquid | Clear dark-yellow liquid | Odorless | Odorless | Odorless |
| Composition C23 | Clear colorless liquid | Clear light-yellow liquid | Clear yellow liquid | Odorless | Odorless | Strong odor |

The results obtained during the evaluation of the organoleptic properties, in particular during prolonged storage at 45° C. for three months, the compositions according to the invention remain odorless and colorless, whereas the comparative compositions exhibit a pronounced odor and/or the appearance of a yellow color which is undesirable in the context of subsequent use in the preparation of a complex cosmetic composition.

C—Preparation of Oil-In-Water Emulsions According to the Invention, Comprising the Compositions According to the Invention and Comparative Compositions An oil-in-water emulsion according to the invention, denoted ($F_{11}$), of which the proportions by weight of its constituents are shown in table 3, and three comparative oil-in-water emulsions, denoted ($F_{21}$) to ($F_{23}$), of which the proportions by weight of their constituents are shown in table 3 below, are prepared. The shared preparation process for the oil-in-water emulsions according to the invention and for the comparative oil-in-water emulsions is as follows:
- the composition to be tested is poured into a beaker, at a temperature of 20° C., under mechanical stirring at 80 revolutions/minute;
- the required amount of the thickening agent Sepinov™ EMT 10 is subsequently added thereto under mechanical stirring at 80 revolutions/minute and at 20° C.;
- the aqueous phase, comprising water and Euxyl™ PE9010, is prepared by mixing in a beaker at a temperature of 20° C.;
- the mixture then obtained is cooled with stirring of deflocculating type at 1500 revolutions per minute for twenty minutes, then emptied out in order to obtain the desired oil-in-water emulsion.

TABLE 3

|  | Emulsion | | | |
|---|---|---|---|---|
|  | ($F_{11}$) | ($F_{21}$) | ($F_{22}$) | ($F_{23}$) |
| Fatty phase |  |  |  |  |
| Sepinov™ EMT10[7] | 1.5% | 1.5% | 1.5% | 1.5% |
| Emogreen™ L19[1] | 0% | 10% | 0% | 0% |
| Lanol™ 2681[3] | 0% | 0% | 10% | 0% |
| Composition C11 | 10% | 0% | 0% | 0% |
| Heptyl Undecylenate (and) C13-C16 Isoparaffin | 0% | 0% | 0% | 10% |
| Aqueous phase |  |  |  |  |
| Water | q. s. 100% | q. s. 100% | q.s. 100% | q. s. 100% |
| Euxyl™ PE 9010[8] | 1% | 1% | 1% | 1% |

[7]Sepinov™ EMT10: Thickening agent (INCI name. Hydroxyethyl Acrylate/Acryloyldimethyltaurate Acrylate Copolymer),
[8]Euxyl™ PE9010 is a preserving agent.

D—Evaluation of the Sensory Properties of Oil-In-Water Emulsions According to the Invention and of Comparative Oil-In-Water Emulsions Principle of the Method Thirteen duly trained and skilled panelists evaluated the criteria of "tackiness" during spreading of the tested emulsion on the skin and of "shininess of the skin" after spreading of the tested emulsion, for oil-in-water emulsions according to the invention and comparative oil-in-water emulsions, taking the emulsion (F11) as reference base.

Procedure

The procedure employed comprises 5 stages, which are as follows:
- stage 1: monitoring and evaluation of the appearance and of the odor of the oil-in-water emulsion tested,
- stage 2: taking in the hand: evaluation of the ease of grasping, and observation of a possible stringy appearance,
- stage 3: spreading of the tested emulsion on the skin by circular application at the surface of the skin, at one and the same speed for 10 rotations, and collection of the feelings perceived at the end of the $10^{th}$ rotation,
- stage 4: continuation of the spreading of the tested emulsion on the skin, still by application of the same circular movement until the absence of film of emulsion on the skin is observed and collection of the feelings perceived, stage 5: collection of the feelings perceived after 1 minute after the end of the spreading. This procedure is carried out at a temperature of 20° C.

Expression of the Results

For each emulsion tested, and for each sensory criterion evaluated, each panelist indicates whether said tested emulsion provides an improved feeling with respect to the reference emulsion ($F_{11}$). All of the evaluations are collected and the data are statistically processed so as to determine the significant nature of a possible difference, improvement or deterioration, between the feeling perceived for the tested emulsion and the reference emulsion.

Results

Criterion of "Tackiness"

Reference emulsion: emulsion ($F_{11}$).

The comparative emulsions ($F_{21}$) to ($F_{23}$) are evaluated according to the protocol defined above and the results obtained are recorded in table 4 below. The increase in the feeling of tackiness with respect to ($F_{11}$) is denoted ">($F_{11}$)" and the decrease in the feeling of tackiness with respect to ($F_{11}$) is denoted "<($F_{11}$)" at each moment of the spreading process.

TABLE 4

| | | | |
|---|---|---|---|
| Stage 3: Evaluation after the first 10 revolutions | <($F_{11}$) | >($F_{11}$) | >($F_{11}$) |
| Stage 4: Evaluation after penetration | <($F_{11}$) | >($F_{11}$) | >($F_{11}$) |
| Stage 5: Evaluation 1 minute after the end of the spreading | <($F_{11}$) | >($F_{11}$) | >($F_{11}$) |

Criterion of "Shininess of the Skin"

Reference emulsion: emulsion ($F_{11}$)

The comparative emulsions (F21) to (F23) are evaluated according to the protocol defined above and the results obtained are recorded in table 4 below. The increase in the shininess of the skin with respect to (F11) is denoted ">(F11)" and its decrease denoted "<($F_{11}$)".

TABLE 5

| | | | |
|---|---|---|---|
| Stage 3: Evaluation after the first 10 revolutions | >($F_{11}$)* | <($F_{11}$) | <($F_{11}$) |
| Stage 4: Evaluation after penetration | >($F_{11}$)* | <($F_{11}$) | <($F_{11}$) |
| Stage 5: Evaluation 1 minute after the end of the spreading | >($F_{11}$)* | <($F_{11}$) | <($F_{11}$) |

*observation of an oily residue on the skin.

Analysis of the Results

The results obtained show an improvement in the sensory properties for the emulsion $F_{(11)}$, in comparison with the emulsions ($F_{21}$) to ($F_{23}$), which makes it possible to have available an emulsion with a decreased feeling of tackiness after spreading and to reduce the shininess of the skin after spreading.

The invention claimed is:

1. A composition comprising, per 100% of its weight:
   a) from 30% by weight to 50% by weight of at least one ester chosen from the elements of the group consisting of:
      glyceryl trioctanoate or glyceryl tridecanoate, or a mixture of glyceryl trioctanoate and glyceryl tridecanoate,
   and of
      the compounds of formula (II):

R—C(=O)—O—R'   (II)

with:
      R—C(=O) represents an acyl radical comprising from eight to ten carbon atoms, and
      R' represents an alkyl radical comprising from one to twenty-two carbon atoms, and
   b) from 50% by weight to 70% by weight of at least one mixture of hydrocarbons, among which at least 94% by weight contain from fifteen to nineteen carbon atoms,
   wherein
      said compounds of the formula (II) are the products of the esterification reaction between an equimolar mixture of octanoic acid and decanoic acid with coconut alcohol, and
      said at least one mixture of hydrocarbons among which at least 94% by weight containing from fifteen to nineteen carbon atoms, comprises per 100% of its weight:
      a proportion by weight of branched alkanes of greater than or equal to 85% and less than or equal to 100%, a proportion by weight of linear alkanes of greater than or equal to 0% and less than or equal to 12%, and a proportion by weight of cycloalkanes of greater than or equal to 0% and less than or equal to 3%.

2. A composition for topical use existing in the form of an emulsion of oil-in-water type, comprising, per 100% of its weight:
   a. from 50% to 90% by weight of a cosmetically acceptable aqueous phase,
   b. from 10% to 50% by weight of a fatty phase comprising, per 100% of its weight:
      $b_{11}$) from 10% to 80% by weight of a composition as defined in claim 1;
      $b_{12}$) from 0.5% to 20% by weight of at least one surface-active agent of oil-in-water type,
      $b_{13}$) from 0% to 89.5% by weight of at least one oil and/or one wax with a composition different from the composition,
   with the sum of the proportions by weight of $b_{11}$), $b_{12}$) and $b_{13}$) equal to 100% of the fatty phase.

3. The composition of claim 1 comprising a mixture of glyceryl trioctanoate and glyceryl tridecanoate, and comprising equal weights of glyceryl trioctanoate and glyceryl tridecanoate.

4. A composition for topical use existing in the form of an emulsion of oil-in water type, comprising, per 100% of its weight:
   a. from 50% to 90% by weight of a cosmetically acceptable aqueous phase,
   b. from 10% to 50% by weight of a fatty phase comprising, per 100% of its weight:
      $b_{11}$) from 10% to 80% by weight of a composition as defined in claim 3;
      $b_{12}$) from 0.5% to 20% by weight of at least one surface-active agent of oil-in-water type,
      $b_{13}$) from 0% to 89.5% by weight of at least one oil and/or one wax with a composition different from the composition,
   with the sum of the proportions by weight of $b_{11}$), $b_{12}$) and $b_{13}$) equal to 100% of the fatty phase.

5. The composition of claim 3, comprising about 30% by weight of the ester mixture and about 70% by weight of the mixture of hydrocarbons.

6. The composition of claim 1 which consists of, per 100% of its weight:
   a) from 30% by weight to 50% by weight of at least one ester chosen from the elements of the group consisting of either:
      a mixture of equal weight of glyceryl trioctanoate and glyceryl tridécanoate, or the products of the esterification reaction between an equimolar mixture of octanoic acid and decanoic acid with coconut alcohol; and b) from 50% by weight to 70% by weight of at least one mixture of hydrocarbons, among which at least 94% by weight contain from fifteen to nineteen carbon atoms, comprising per 100% of its weight:
a proportion by weight of branched alkanes of greater than or equal to 80% and less than or equal to 100%, a proportion by weight of linear alkanes of greater than or equal to 0% and less than or equal to 15%, and a proportion by weight of cycloalkanes of greater than or equal to 0% and less than or equal to 5%.

7. A composition for topical use existing in the form of an emulsion of oil-in-water type, comprising, per 100% of its weight:
a. from 50% to 90% by weight of a cosmetically acceptable aqueous phase,
b. from 10% to 50% by weight of a fatty phase comprising, per 100% of its weight:
$b_{11}$) from 10% to 80% by weight of a composition as defined in claim 6;
$b_{12}$) from 0.5% to 20% by weight of at least one surface-active agent of oil-in-water type,
$b_{13}$) from 0% to 89.5% by weight of at least one oil and/or one wax with a composition different from the composition,
with the sum of the proportions by weight of $b_{11}$), $b_{12}$) and $b_{13}$) equal to 100% of the fatty phase.

8. The composition of claim 1, wherein the ester is the product of the esterification reaction between an equimolar mixture of octanoic acid and decanoic acid with coconut alcohol.

9. The composition of claim 8, comprising about 30% by weight of the ester product and about 70% by weight of the mixture of hydrocarbons.

10. A composition for topical use existing in the form of an emulsion of oil in water type, comprising, per 100% of its weight:
a. from 50% to 90% by weight of a cosmetically acceptable aqueous phase,
b. from 10% to 50% by weight of a fatty phase comprising, per 100% of its weight:
$b_{11}$) from 10% to 80% by weight of a composition as defined in claim 8;
$b_{12}$) from 0.5% to 20% by weight of at least one surface-active agent of oil-in-water type,
$b_{13}$) from 0% to 89.5% by weight of at least one oil and/or one wax with a composition different from the composition,
with the sum of the proportions by weight of $b_{11}$), $b_{12}$) and $b_{13}$) equal to 100% of the fatty phase.

11. The composition of claim 1, comprising about 30% by weight of the ester and about 70% by weight of the mixture of hydrocarbons.

12. A composition for topical use existing in the form of an emulsion of oil-in water type, comprising, per 100% of its weight:
a. from 50% to 90% by weight of a cosmetically acceptable aqueous phase,
b. from 10% to 50% by weight of a fatty phase comprising, per 100% of its weight:
$b_{11}$) from 10% to 80% by weight of a composition as defined in claim 11;
$b_{12}$) from 0.5% to 20% by weight of at least one surface-active agent of oil-in-water type,
$b_{13}$) from 0% to 89.5% by weight of at least one oil and/or one wax with a composition different from the composition,
with the sum of the proportions by weight of $b_{11}$), $b_{12}$) and $b_{13}$) equal to 100% of the fatty phase.

13. The composition of claim 1, wherein the mixture of hydrocarbons comprises:
a proportion by weight of branched alkanes of greater than or equal to 95%,
a proportion by weight of linear alkanes of less than or equal to 5%, and
a proportion by weight of cycloalkanes of less than or equal to 1%.

14. The composition of claim 13, comprising about 30% by weight of the ester and about 70% by weight of the mixture of hydrocarbons.

* * * * *